US012642543B2

(12) United States Patent (10) Patent No.: US 12,642,543 B2
Gamez et al. (45) **Date of Patent: \*Jun. 2, 2026**

(54) STERILE FIELD CLOT CATCHER DEVICE, MODULE AND METHODS

(71) Applicant: Von Vascular, Inc., Weston, FL (US)

(72) Inventors: Victor Gamez, Fort Lauderdale, FL
(US); Manning J. Hanser, Weston, FL
(US); Alfonso Hermida, Miramar, FL
(US)

(73) Assignee: Von Vascular, Inc., Weston, FL (US)

( \* ) Notice: Subject to any disclaimer, the term of this
patent is extended or adjusted under 35
U.S.C. 154(b) by 249 days.

This patent is subject to a terminal dis-
claimer.

(21) Appl. No.: 18/373,955

(22) Filed: Sep. 27, 2023

(65) Prior Publication Data

US 2024/0138858 A1 May 2, 2024

Related U.S. Application Data

(63) Continuation-in-part of application No. 18/123,973,
filed on Mar. 20, 2023.

(Continued)

(51) Int. Cl.
*A61B 17/22* (2006.01)
*A61B 17/00* (2006.01)
(52) U.S. Cl.
CPC .... *A61B 17/22* (2013.01); *A61B 2017/00292*
(2013.01); *A61B 2017/22079* (2013.01)
(58) Field of Classification Search
CPC .............. A61B 17/22; A61B 17/00234; A61B
2017/00292; A61B 2017/22079;
(Continued)

(56) References Cited

U.S. PATENT DOCUMENTS 3,589,363 A 6/1971 Banko et al.
3,955,574 A 5/1976 Rubensten
(Continued)

FOREIGN PATENT DOCUMENTS

CN 118251244 A 6/2024
EP 0777504 B1 10/1998
(Continued)

OTHER PUBLICATIONS

Baek, Hong-Gyu et al. "Craniotomy and Membranectomy for
Treatment of Organized Chronic Subdural Hematoma," Korean
Journal of Neurotrauma, 2018 (12 pages).
(Continued)

*Primary Examiner* — Katherine M Rodjom

(57) ABSTRACT

A clot capture device assists a surgeon or medical technician
to directly see a degree of blood displacement and what type
of clot is being or has been extracted, and preferably, all on
the sterile field at convenient reach and visual observation
by the user (physician or technician), and without cessation
of a clot removal procedure. Aspirated blood and a retrieved
clot or clots are ejected and deposited on a generally
horizontally oriented porous filter and/or foraminous
strainer in a co-compartment, for separation thereof. The
clot or clots stay in the co-compartment atop the strainer/
filter, while extracted blood drains into a blood collection
compartment below.

16 Claims, 4 Drawing Sheets

Related U.S. Application Data

(60) Provisional application No. 63/474,167, filed on Jul. 26, 2022, provisional application No. 63/335,168, filed on Apr. 26, 2022, provisional application No. 63/325,778, filed on Mar. 31, 2022, provisional application No. 63/321,706, filed on Mar. 20, 2022.

(58) Field of Classification Search
CPC A61B 2017/00561; A61B 2017/00123; A61B 2017/00137; A61B 2017/00199; A61B 2017/00778; A61B 2217/005; A61M 1/64; A61M 1/65; A61M 1/68
See application file for complete search history.

(56) References Cited

U.S. PATENT DOCUMENTS

| | | | |
|---|---|---|---|
| 4,798,580 A | 1/1989 | DeMeo et al. |
| 4,832,685 A | 5/1989 | Haines |
| 4,921,477 A | 5/1990 | Davis |
| 4,930,997 A | 6/1990 | Bennett |
| 4,935,005 A | 6/1990 | Haines |
| 5,125,891 A | 6/1992 | Hossain et al. |
| 5,256,233 A | 10/1993 | Winter et al. |
| 5,267,956 A | 12/1993 | Beuchat |
| 5,364,342 A | 11/1994 | Beuchat |
| 5,419,774 A | 5/1995 | Willard et al. |
| 5,454,795 A | 10/1995 | Samson |
| 5,460,490 A | 10/1995 | Carr et al. |
| 5,496,270 A | 3/1996 | Nettekoven |
| 5,827,229 A | 10/1998 | Auth et al. |
| 5,938,587 A | 8/1999 | Taylor et al. |
| 6,022,747 A | 2/2000 | Gherson et al. |
| 6,071,267 A | 6/2000 | Zamierowski |
| 6,115,860 A | 9/2000 | Vrzalik |
| D445,804 S | 7/2001 | Tsai |
| 6,306,163 B1 | 10/2001 | Fitz |
| 6,387,065 B1 | 5/2002 | Tumey |
| 6,468,237 B1 | 10/2002 | Lina |
| 6,517,513 B1 | 2/2003 | Covington |
| 6,547,756 B1 | 4/2003 | Greter et al. |
| 6,673,028 B1 | 1/2004 | Argenta et al. |
| 6,858,024 B1 | 2/2005 | Berg et al. |
| 6,904,631 B2 | 6/2005 | Vrzalik et al. |
| 6,942,634 B2 | 9/2005 | Odland |
| 7,004,915 B2 | 2/2006 | Boynton et al. |
| D520,023 S | 5/2006 | Goto et al. |
| 7,108,683 B2 | 9/2006 | Zamierowski |
| 7,198,046 B1 | 4/2007 | Argenta et al. |
| 7,276,052 B2 | 10/2007 | Kobayashi et al. |
| 7,284,965 B2 | 10/2007 | Adahan |
| D573,609 S | 7/2008 | Bilger |
| 7,410,491 B2 | 8/2008 | Hopkins et al. |
| 7,618,382 B2 | 11/2009 | Vogel et al. |
| 7,662,109 B2 | 2/2010 | Hibner |
| 7,666,161 B2 | 2/2010 | Nash et al. |
| 7,713,235 B2 | 5/2010 | Torrance et al. |
| 7,717,853 B2 | 5/2010 | Nita |
| 7,828,748 B2 | 11/2010 | Hibner |
| 7,842,009 B2 | 11/2010 | Torrance et al. |
| 7,854,707 B2 | 12/2010 | Hibner et al. |
| 7,867,173 B2 | 1/2011 | Hibner et al. |
| 7,896,817 B2 | 3/2011 | Garrison |
| 7,918,804 B2 | 4/2011 | Monson et al. |
| 7,918,822 B2 | 4/2011 | Kumar et al. |
| 7,931,659 B2 | 4/2011 | Bose et al. |
| 7,938,786 B2 | 5/2011 | Ritchie et al. |
| 7,959,608 B2 | 6/2011 | Nash et al. |
| 7,981,049 B2 | 7/2011 | Ritchie et al. |
| 8,038,627 B2 | 10/2011 | Hibner |
| 8,070,735 B2 | 12/2011 | Koch et al. |
| 8,075,510 B2 | 12/2011 | Aklog et al. |
| 8,118,755 B2 | 2/2012 | Hibner et al. |
| 8,235,955 B2 | 8/2012 | Blott et al. |
| 8,251,916 B2 | 8/2012 | Speeg et al. |
| 8,333,796 B2 | 12/2012 | Tompkins |
| 8,337,475 B2 | 12/2012 | Christensen et al. |
| 8,366,735 B2 | 2/2013 | Bose et al. |
| 8,394,078 B2 | 3/2013 | Torrance et al. |
| 8,414,534 B2 | 4/2013 | Bandhauer et al. |
| 8,460,312 B2 | 6/2013 | Bose et al. |
| 8,465,467 B2 | 6/2013 | Gao |
| 8,480,595 B2 | 7/2013 | Speeg et al. |
| 8,506,512 B2 | 8/2013 | Aklog et al. |
| 8,591,453 B2 | 11/2013 | Stubkjaer et al. |
| 8,613,717 B2 | 12/2013 | Aklog et al. |
| 8,632,498 B2 | 1/2014 | Rimsa et al. |
| 8,657,785 B2 | 2/2014 | Torrance et al. |
| 8,679,150 B1 | 3/2014 | Janardhan et al. |
| 8,690,907 B1 | 4/2014 | Janardhan et al. |
| 8,702,623 B2 | 4/2014 | Parihar et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,721,676 B1 | 5/2014 | Janardhan et al. |
| 8,721,677 B1 | 5/2014 | Janardhan et al. |
| 8,733,618 B1 | 5/2014 | Janardhan et al. |
| 8,734,374 B2 | 5/2014 | Aklog et al. |
| 8,737,017 B1 | 5/2014 | Abe |
| 8,747,432 B1 | 6/2014 | Janardhan et al. |
| 8,753,371 B1 | 6/2014 | Janardhan et al. |
| 8,758,315 B2 | 6/2014 | Chen et al. |
| 8,783,151 B1 | 7/2014 | Janardhan et al. |
| 8,789,452 B1 | 7/2014 | Janardhan et al. |
| 8,795,244 B2 | 8/2014 | Randolph et al. |
| 8,803,030 B1 | 8/2014 | Janardhan et al. |
| 8,816,247 B1 | 8/2014 | Janardhan et al. |
| D712,933 S | 9/2014 | DeOreo et al. |
| 8,852,219 B2 | 10/2014 | Wulfman et al. |
| 8,852,227 B1 | 10/2014 | Janardhan et al. |
| 8,859,934 B1 | 10/2014 | Janardhan et al. |
| 8,872,068 B1 | 10/2014 | Janardhan et al. |
| 8,882,797 B2 | 11/2014 | Janardhan et al. |
| 8,895,891 B2 | 11/2014 | Janardhan et al. |
| 8,904,914 B2 | 12/2014 | Janardhan et al. |
| 8,910,555 B2 | 12/2014 | Janardhan et al. |
| 8,911,487 B2 | 12/2014 | Bennett |
| 8,920,402 B2 | 12/2014 | Nash et al. |
| 8,932,320 B1 | 1/2015 | Janardhan et al. |
| 9,034,007 B2 | 5/2015 | Janardhan |
| 9,078,964 B2 | 7/2015 | Schuman |
| 9,095,326 B2 | 8/2015 | Ritchie et al. |
| 9,119,656 B2 | 9/2015 | Bose et al. |
| 9,125,731 B2 | 9/2015 | Ross et al. |
| 9,179,931 B2 | 11/2015 | Janardhan et al. |
| 9,179,995 B2 | 11/2015 | Janardhan et al. |
| 9,186,444 B2 | 11/2015 | Lonky et al. |
| 9,241,699 B1 | 1/2016 | Kume et al. |
| 9,265,512 B2 | 2/2016 | Garrison et al. |
| 9,314,324 B2 | 4/2016 | Janardhan et al. |
| 9,332,998 B2 | 5/2016 | Ray et al. |
| 9,332,999 B2 | 5/2016 | Ray et al. |
| 9,345,457 B2 | 5/2016 | Speeg et al. |
| 9,402,938 B2 | 8/2016 | Aklog et al. |
| RE46,135 E | 9/2016 | Hibner |
| 9,445,831 B2 | 9/2016 | Mark |
| 9,526,865 B2 | 12/2016 | Quick |
| 9,532,792 B2 | 1/2017 | Galdonik et al. |
| 9,561,129 B2 | 2/2017 | Ross et al. |
| 9,561,345 B2 | 2/2017 | Garrison et al. |
| 9,592,068 B2 | 3/2017 | Janardhan et al. |
| 9,615,832 B2 | 4/2017 | Bose et al. |
| 9,655,633 B2 | 5/2017 | Leynov et al. |
| 9,693,789 B2 | 7/2017 | Garrison et al. |
| 9,750,524 B2 | 9/2017 | Janardhan et al. |
| 9,820,761 B2 | 11/2017 | Garrison et al. |
| 9,833,251 B2 | 12/2017 | Janardhan et al. |
| 9,855,374 B2 | 1/2018 | Sherman et al. |
| 9,883,854 B2 | 2/2018 | Mak |
| 9,883,877 B2 | 2/2018 | Look et al. |
| 9,901,435 B2 | 2/2018 | Janardhan et al. |
| 9,915,674 B2 | 3/2018 | Zordan |
| 9,943,321 B2 | 4/2018 | Nita |
| 9,956,326 B2 | 5/2018 | Ramella et al. |
| 9,999,710 B2 | 6/2018 | Ross et al. |

(56) References Cited

U.S. PATENT DOCUMENTS

| | | | |
|---|---|---|---|
| 10,219,814 | B2 | 3/2019 | Feltyberger et al. |
| 10,238,789 | B2 | 3/2019 | Kuntz et al. |
| 10,251,739 | B2 | 4/2019 | Janardhan et al. |
| D847,864 | S | 5/2019 | Janardhan et al. |
| D847,865 | S | 5/2019 | Janardhan et al. |
| D847,866 | S | 5/2019 | Janardhan et al. |
| D850,490 | S | 6/2019 | Janardhan et al. |
| 10,335,260 | B2 | 7/2019 | Janardhan et al. |
| 10,342,655 | B2 | 7/2019 | Janardhan et al. |
| 10,390,926 | B2 | 8/2019 | Janardhan et al. |
| 10,463,468 | B2 | 11/2019 | Janardhan et al. |
| 10,517,617 | B2 | 12/2019 | Aklog et al. |
| 10,531,883 | B1 | 1/2020 | Deville et al. |
| 10,722,253 | B2 | 7/2020 | Deville et al. |
| 10,751,159 | B2 | 8/2020 | Janardhan et al. |
| D896,847 | S | 9/2020 | Janardhan et al. |
| 10,799,669 | B2 | 10/2020 | Chou et al. |
| 10,946,123 | B2 | 3/2021 | Christensen et al. |
| 11,020,133 | B2 | 6/2021 | Wilson et al. |
| 11,052,006 | B2 | 7/2021 | Tanaka |
| 11,065,019 | B1 | 7/2021 | Chou et al. |
| 11,071,812 | B2 | 7/2021 | Raman et al. |
| 11,096,703 | B2 | 8/2021 | Panian |
| 11,096,712 | B2 | 8/2021 | Teigen et al. |
| 11,147,949 | B2 | 10/2021 | Yang et al. |
| 11,197,683 | B1 | 12/2021 | Teigen et al. |
| 11,197,977 | B2 | 12/2021 | Mullins et al. |
| 11,298,144 | B2 | 4/2022 | Janardhan et al. |
| 11,337,712 | B2 | 5/2022 | Teigen et al. |
| 11,337,855 | B2 | 5/2022 | Bandhauer et al. |
| 11,399,861 | B2 | 8/2022 | Stulen et al. |
| 11,400,255 | B1 | 8/2022 | Chou et al. |
| 11,406,402 | B2 | 8/2022 | Deville et al. |
| 11,432,835 | B2 | 9/2022 | Shaffer et al. |
| 11,436,806 | B1 | 9/2022 | Katz et al. |
| 11,490,911 | B2 | 11/2022 | Panian |
| 11,497,523 | B2 | 11/2022 | Trosper et al. |
| 11,523,830 | B2 | 12/2022 | Tompkins et al. |
| 11,547,426 | B2 | 1/2023 | Deville et al. |
| 11,553,935 | B2 | 1/2023 | Buck et al. |
| 11,586,276 | B2 | 2/2023 | Winold et al. |
| 11,638,660 | B2 | 5/2023 | Balkenbush et al. |
| 11,730,499 | B1 | 8/2023 | Thio et al. |
| 11,744,600 | B2 | 9/2023 | Look et al. |
| 11,759,219 | B2 | 9/2023 | Teigen et al. |
| 11,844,891 | B2 | 12/2023 | Hanani et al. |
| 11,890,024 | B2 | 2/2024 | Panian |
| 11,918,240 | B2 | 3/2024 | Deville et al. |
| 12,005,228 | B2 | 6/2024 | Ofek et al. |
| 12,076,225 | B2 | 9/2024 | Erbey et al. |
| 12,201,311 | B2 | 1/2025 | Teigen et al. |
| 12,208,196 | B2 | 1/2025 | Quintanar |
| 12,251,119 | B2 | 3/2025 | Naglreiter et al. |
| 2003/0069549 | A1 | 4/2003 | MacMahon et al. |
| 2005/0085769 | A1 | 4/2005 | MacMahon et al. |
| 2005/0124969 | A1 | 6/2005 | Fitzgerald et al. |
| 2006/0058837 | A1 | 3/2006 | Bose et al. |
| 2007/0038100 | A1 | 2/2007 | Nita |
| 2007/0135832 | A1 | 6/2007 | Wholey et al. |
| 2007/0166180 | A1 | 7/2007 | Adahan |
| 2007/0239261 | A1 | 10/2007 | Bose et al. |
| 2007/0269321 | A1 | 11/2007 | Adahan |
| 2008/0004545 | A1 | 1/2008 | Garrison |
| 2008/0015478 | A1 | 1/2008 | Bose |
| 2008/0051708 | A1 | 2/2008 | Kumar et al. |
| 2008/0056915 | A1 | 3/2008 | Adahan |
| 2008/0319355 | A1 | 12/2008 | Nita |
| 2009/0005747 | A1 | 1/2009 | Michaels et al. |
| 2009/0030400 | A1 | 1/2009 | Bose et al. |
| 2009/0187131 | A1 | 7/2009 | Fitzgerald et al. |
| 2009/0318892 | A1 | 12/2009 | Aboytes et al. |
| 2010/0114017 | A1 | 5/2010 | Lenker et al. |
| 2010/0150991 | A1 | 6/2010 | Bernstein |
| 2010/0191178 | A1 | 7/2010 | Ross et al. |
| 2010/0204672 | A1 | 8/2010 | Lockhart et al. |
| 2010/0217276 | A1 | 8/2010 | Garrison et al. |
| 2010/0280434 | A1 | 11/2010 | Raney et al. |
| 2011/0137231 | A1 | 6/2011 | Sorensen et al. |
| 2011/0160621 | A1 | 6/2011 | Nita |
| 2011/0160761 | A1 | 6/2011 | Ferrera et al. |
| 2011/0184454 | A1 | 7/2011 | Barry et al. |
| 2011/0213290 | A1 | 9/2011 | Chin et al. |
| 2011/0213392 | A1 | 9/2011 | Aklog et al. |
| 2011/0264133 | A1 | 10/2011 | Hanlon et al. |
| 2011/0313328 | A1 | 12/2011 | Nita |
| 2011/0319927 | A1 | 12/2011 | Nita |
| 2012/0078140 | A1 | 3/2012 | Nita |
| 2012/0078285 | A1 | 3/2012 | Griffin |
| 2012/0150147 | A1 | 6/2012 | Leynov et al. |
| 2012/0283563 | A1 | 11/2012 | Moore et al. |
| 2012/0330196 | A1 | 12/2012 | Nita |
| 2013/0304082 | A1 | 11/2013 | Aklog et al. |
| 2013/0324882 | A1 | 12/2013 | Mescher |
| 2014/0039343 | A1 | 2/2014 | Mescher et al. |
| 2014/0128907 | A1 | 5/2014 | Hui et al. |
| 2014/0180377 | A1 | 6/2014 | Bose et al. |
| 2014/0271273 | A1 | 9/2014 | Carpenter |
| 2014/0276897 | A1 | 9/2014 | Rockley et al. |
| 2014/0277082 | A1 | 9/2014 | Janardhan et al. |
| 2015/0028005 | A1 | 1/2015 | Janardhan et al. |
| 2015/0032121 | A1 | 1/2015 | Janardhan et al. |
| 2015/0032146 | A1 | 1/2015 | Janardhan et al. |
| 2015/0032147 | A1 | 1/2015 | Janardhan et al. |
| 2015/0196304 | A1 | 7/2015 | Rabkin et al. |
| 2015/0238303 | A1 | 8/2015 | Janardhan |
| 2015/0359666 | A1 | 12/2015 | Zacharias |
| 2016/0058614 | A1 | 3/2016 | Ross et al. |
| 2016/0120557 | A1 | 5/2016 | Goddard et al. |
| 2016/0166265 | A1 | 6/2016 | Nita |
| 2017/0021072 | A1 | 1/2017 | Forsell |
| 2017/0105743 | A1 | 4/2017 | Vale et al. |
| 2017/0112981 | A1 | 4/2017 | Friedman et al. |
| 2017/0136158 | A1 | 5/2017 | Culhane et al. |
| 2017/0147765 | A1 | 5/2017 | Mehta |
| 2017/0151032 | A1 | 6/2017 | Loisel |
| 2017/0165001 | A1 | 6/2017 | Lyttle |
| 2017/0181760 | A1 | 6/2017 | Look et al. |
| 2017/0181761 | A1 | 6/2017 | Janardhan et al. |
| 2017/0333060 | A1 | 11/2017 | Panian |
| 2017/0360469 | A1 | 12/2017 | Janardhan et al. |
| 2018/0049921 | A1 | 2/2018 | Sorensen et al. |
| 2018/0085136 | A1 | 3/2018 | Janardhan et al. |
| 2018/0197633 | A1 | 7/2018 | Mehta |
| 2018/0228502 | A1 | 8/2018 | Shaffer et al. |
| 2018/0256797 | A1 | 9/2018 | Schenck et al. |
| 2018/0263646 | A1 | 9/2018 | Loisel |
| 2018/0338770 | A1 | 11/2018 | Mogi et al. |
| 2018/0339130 | A1 | 11/2018 | Ogle |
| 2019/0133745 | A1 | 5/2019 | Janardhan et al. |
| 2019/0142567 | A1 | 5/2019 | Janardhan et al. |
| 2019/0142568 | A1 | 5/2019 | Janardhan et al. |
| 2019/0167406 | A1 | 6/2019 | Janardhan et al. |
| 2020/0046368 | A1 | 2/2020 | Merritt et al. |
| 2020/0297362 | A1 | 9/2020 | Deville et al. |
| 2020/0397956 | A1 | 12/2020 | Luxon et al. |
| 2020/0397957 | A1* | 12/2020 | Teigen ................... A61M 1/77 |
| 2021/0093344 | A1 | 4/2021 | Janardhan et al. |
| 2021/0137540 | A1 | 5/2021 | Panian |
| 2021/0186534 | A1 | 6/2021 | Hunt et al. |
| 2021/0378691 | A1 | 12/2021 | Panian |
| 2022/0054151 | A1 | 2/2022 | Shifflette |
| 2022/0168000 | A1 | 6/2022 | Nagireiter et al. |
| 2022/0168001 | A1 | 6/2022 | Naglreiter et al. |
| 2022/0168002 | A1 | 6/2022 | Naglreiter et al. |
| 2022/0280171 | A1 | 9/2022 | Teigen et al. |
| 2022/0296260 | A1 | 9/2022 | Janardhan et al. |
| 2022/0296261 | A1 | 9/2022 | Panian |
| 2022/0313288 | A1 | 10/2022 | Janardhan et al. |
| 2022/0323096 | A1* | 10/2022 | Naglreiter .............. A61B 17/22 |
| 2022/0330958 | A1 | 10/2022 | Mobley |
| 2022/0378449 | A1 | 12/2022 | Look et al. |
| 2023/0000510 | A1 | 1/2023 | Brady et al. |
| 2023/0026412 | A1 | 1/2023 | Teigen et al. |
| 2023/0043096 | A1 | 2/2023 | Panian |

(56) References Cited

U.S. PATENT DOCUMENTS

| | | |
|---|---|---|
| 2023/0063577 A1 | 3/2023 | Pons |
| 2023/0099283 A1 | 3/2023 | Deville et al. |
| 2023/0100426 A1 | 3/2023 | Deville et al. |
| 2023/0112635 A1 | 4/2023 | Panian |
| 2023/0181200 A1 | 6/2023 | Deville et al. |
| 2023/0240694 A1 | 8/2023 | Panian |
| 2023/0263545 A1 | 8/2023 | Wilcox et al. |
| 2023/0364319 A1 | 11/2023 | Vale et al. |
| 2024/0000469 A1 | 1/2024 | Teigen et al. |
| 2024/0148957 A1 | 5/2024 | Brown et al. |
| 2024/0148958 A1 | 5/2024 | Reyes et al. |
| 2024/0277914 A1 | 8/2024 | Vale et al. |
| 2024/0285292 A1 | 8/2024 | Hanser et al. |
| 2025/0064466 A1 | 2/2025 | Hanser et al. |
| 2025/0064467 A1 | 2/2025 | Hanser et al. |
| 2025/0288306 A1 | 9/2025 | Hanser et al. |

FOREIGN PATENT DOCUMENTS

| | | | |
|---|---|---|---|
| EP | 3123964 B1 | 4/2019 | |
| WO | WO 2006/117207 A1 | 11/2006 | |
| WO | WO 2012/057881 A1 | 5/2012 | |
| WO | WO 2014/151209 A1 | 9/2014 | |
| WO | WO 2015/157330 A1 | 10/2015 | |
| WO | WO 2016/018448 A1 | 2/2016 | |
| WO | WO 2017/134462 A1 | 8/2017 | |
| WO | WO 2021/108371 | 6/2021 | |
| WO | WO 2023/220633 A2 | 11/2023 | |
| WO | WO 2024/016004 A2 | 1/2024 | |

OTHER PUBLICATIONS

Lee, Kyeong-Seok et al. "Acute-on-Chronic Subdural Hematoma: Not Uncommon Events," Journal of Korean Neurosurgical Society, 2011 (13 pages).

Majovsky, Martin et al. "Burr-Hole Evacuation of Chronic Subdural Hematoma: Biophysically and Evidence-Based Technique Improvement," Journal of Neurosciences in Rural Practice, 2018 (6 pages).

Manivannan, Susruta et al. "Acute subdural haematoma in the elderly: to operate or not to operate? A systematic review and meta-analysis of outcomes following surgery," BMJ Open, 2021 (13 pages).

Peng, Deqing et al. "External drains versus no drains after burr-hole evacuation for the treatment of chronic subdural haematoma in adults," Cochrane Database of Systematic Reviews, Chochrane Library, Aug. 31, 2016 (56 pages).

Xu, Min et al. "Minimally Invasive Surgery in Chronic Subdural Hematoma: Prognosis and Recurrence Factors of 516 Cases in a Single Center," Journal of Clinical Medicine, 2022 (8 pages).

International Search Report and Written Opinion for PCT/US2024/015950, mailed Aug. 7, 2024.

Office Action for U.S. Appl. No. 18/596,868, mailed Sep. 10, 2024.

Office Action for U.S. Appl. No. 18/949,280, mailed Dec. 16, 2024.

Office Action for U.S. Appl. No. 19/223,433, mailed Aug. 6, 2025.

Office Action for U.S. Appl. No. 18/123,973, mailed Sep. 10, 2025.

International Search Report and Written Opinion for PCT/US2025/037893, mailed Oct. 28, 2025.

Mathews, S. Jay et al. "The Akura Thrombectomy Catheter System for the Treatment of VTE," Insert to Endovascular Today, vol. 23, No. 1, Jan. 2024 (4 pages).

* cited by examiner

11a

16

15

15

11a

STERILE FIELD CLOT CATCHER DEVICE, MODULE AND METHODS

CROSS REFERENCE TO RELATED APPLICATIONS

This application claims the benefit of U.S. application Ser. No. 18/123,973 filed Mar. 20, 2023 entitled ADAPTIVE PRESSURE-CYCLICAL ASPIRATION DEVICE AND METHODS.

BACKGROUND OF THE INVENTION

The present disclosures relate, inter alia, to improved acute ischemic event therapies, and equipment and methods for implementing same to effectively and efficiently remove a clot occluding a vessel in a facilitated manner And more particularly, to methods and devices which advantageously permit examination and identification analysis of a nature of a retrieved clot while remaining on a sterile field without requiring cessation of an extraction process.

The current disclosures relate generally to a system that employs thrombotic extraction strategies for removing a clot occluding a blood vessel with applied aspiration via an inserted clot-extracting catheter in an occluded vessel.

Heretofore, conventional clot aspiration systems typically have clot retrieval/collection devices disposed in-line with the suction path. This requires the user to stop the suction pump in order to retrieve the clot. Such approaches by other systems means that clot retrieval from the clot catcher for observation, examination and identification requires a stoppage of the clot removal aspiration process. This results in critical delay in time sensitive therapeutic procedures often to the detriment of the patient being treated.

It would therefore be highly desirable to create a system and method which can be effective to allow a physician and/or qualified technician to retrieve the extracted clot or clots without having to halt the aspiration process, and which broadly addresses and overcomes these and other drawbacks of prior art approaches.

SUMMARY OF THE INVENTION

In accordance with these and other objects of the invention, there is provided a thrombotic extraction system which advantageously includes a method and structural adaptation, in a form, for example, which is embodied to include an independent device or integrated module that permits examination of an extracted blood clot or clots without requiring a pause in the treatment process while advantageously remaining on the sterile field.

In accordance with an advantageous embodiment, a clot catcher (or alternatively referred to herein as a "clot collector") is built into an advantageously sterile blood collection canister or collection compartment in order to help the surgeon or medical technician to directly see a degree of blood displacement and what type of clot is being or has been extracted. More preferably, all on the sterile field at convenient reach and visual observation by the user (physician or technician).

In accordance with an embodiment of the invention, aspirated blood and a retrieved clot or clots are ejected and deposited on a porous filter and/or foraminous strainer in a co-compartment, for separation thereof. The clot or clots stay in the co-compartment atop the strainer/filter, while extracted blood drains into a reservoir/canister/compartment below. According to an advantageous embodiment, the reservoir/canister/compartment is sterile.

According to a particularly advantageous embodiment, the reservoir/canister/compartment, referred to herein generically as a "blood collection chamber," can hold over 1000 cc of extracted blood on the sterile field.

A clot capture device (clot catcher) is advantageously fully integrated with a blood collection pump and control assembly comprising an aspiration pump and also optionally various controls, that allows the capture and immediate removal of the aspired clot without having to exit the sterile field or halt a collection process.

The clot catcher optionally includes a lid over the co-compartment disposed above the strainer, conveniently provided in a form of a transparent window, that can be removed or opened for collection of the extracted clot for subsequent examination and analysis. The clot catcher co-compartment bottom includes a perforated strainer provided for example in a form of a sieve or porous filter, etc., referred to generically herein by the term "strainer" in order to allow the passage of blood to a downstream side thereof while retaining the extracted clot on an upstream side above the filter/strainer.

An integrated extraction pump can also be optionally operated with the cover of the clot catcher completely removed or in an open state for even faster and easier clot removal by the user.

While several embodiments of the present disclosure are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, Within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, Whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various medications are possible within the scope of the claims. Accordingly, the claims are intended to cover all such equivalents.

Reference throughout this specification to "one embodiment," "an embodiment," or similar language means that a particular feature, structure, or characteristic described in connection with the embodiment is included in at least one embodiment of the present invention.

Thus, appearances of the phrases "in one embodiment," "in an embodiment," and similar throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well—known structures, materials, and so forth. In other instances, well—known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method.

Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method.

Additionally, the order in which a particular method occurs may or may not strictly adhere to the order of the corresponding steps or methodologies shown.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be personnel in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all medications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core i5, Intel Core I & Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e. g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e. g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Various preferred embodiments are described herein with references to the drawings in which merely illustrative views are offered for consideration, whereby:

Corresponding reference characters indicate corresponding components throughout the several views of the drawings. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

The above, and other objects, features and advantages of the present invention will become apparent from the following description read in conjunction with the accompanying drawings.

Features, aspects, and advantages are described below with reference to the drawings, which are intended to illustrate, but not to limit, the invention. In the drawings, like reference characters denote corresponding features consistently throughout similar embodiments.

Corresponding reference characters indicate corresponding components throughout the several views of the drawing. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention.

Also, common but well-understood elements that are useful or necessary in a commercially feasible embodiment are often not depicted in order to facilitate a less obstructed view of these various embodiments of the present invention.

DETAILED DESCRIPTION OF THE PREFERRED EMBODIMENT

Figure 1A:
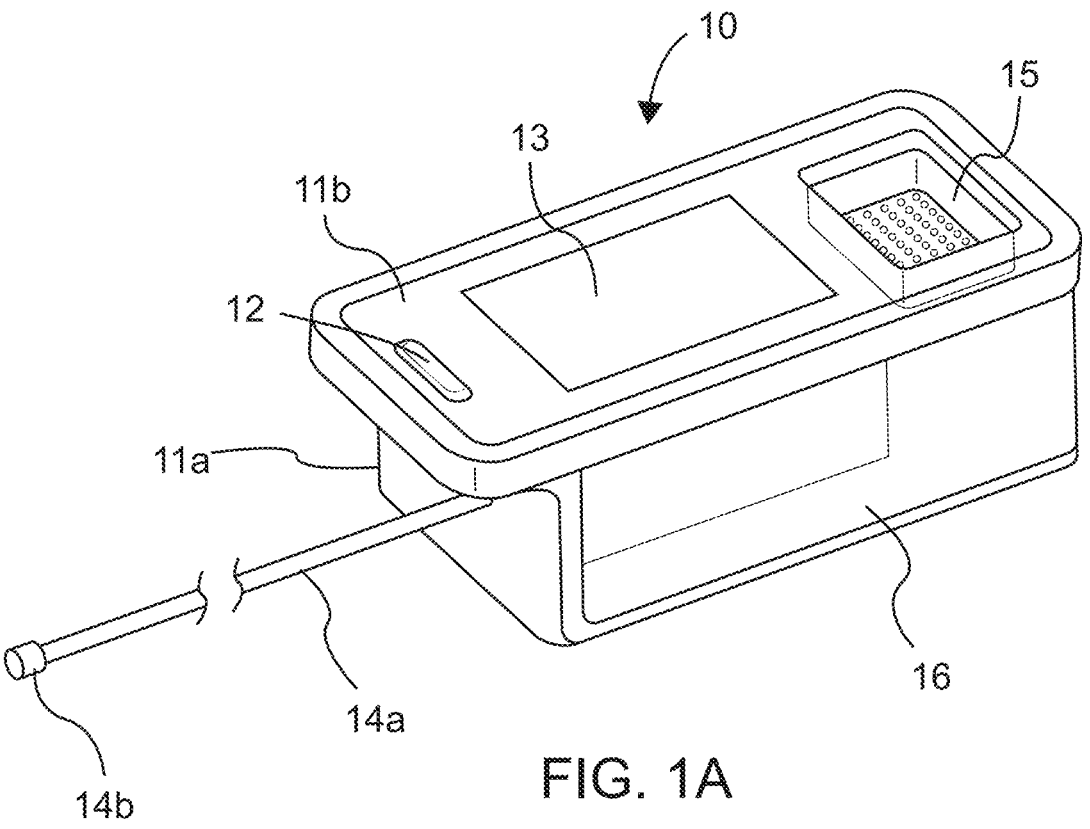
FIG. 1A is a perspective view depicting an example of a pump system incorporating a clot catcher as an integral sub-component module in accordance with an embodiment of the invention.
Figure 1B:
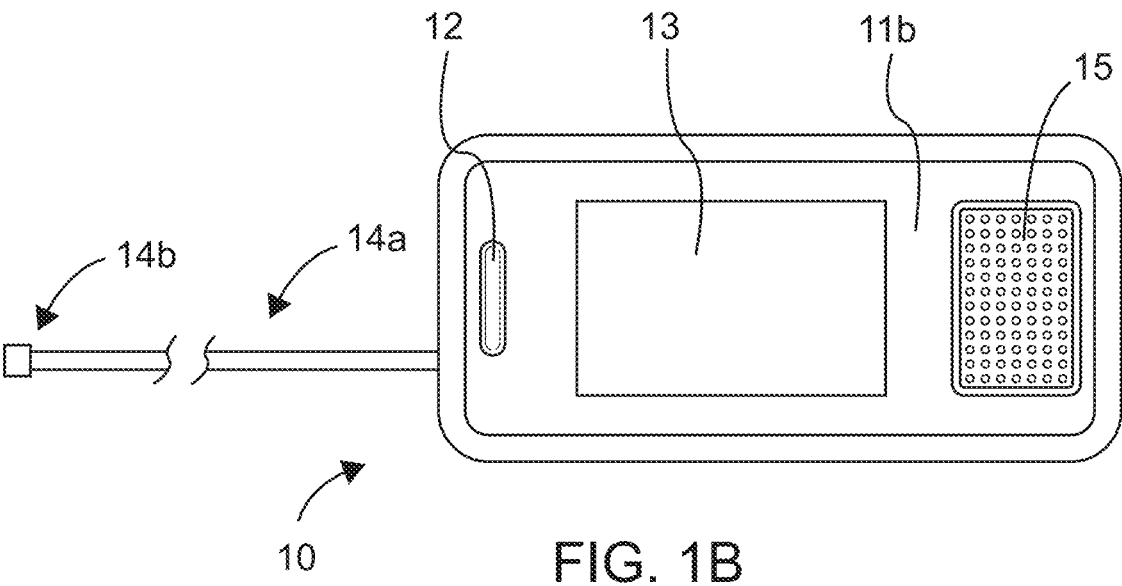
FIG. 1B is a top plan view of the pump system including the clot catcher of the embodiment of FIG. 1A.

Referring now to the figures, a pump system incorporating a clot catcher as an integral sub-component/module in accordance with an embodiment of the invention is depicted generally at 10 in FIGS. 1A and 1B.

Pump system 10 according to the exemplary embodiment depicted in FIGS. 1A and 1B optionally includes a housing comprised of a housing bottom 11 *a* and a housing top 11*b*. A control button or switch 12 is advantageously provided to permit convenient access by the operator/user to optionally selectively control an operating mode of pump system 10. A touch screen 13 is also optionally provided to control various operational aspects of the pump system 10.

Connected to the pump system is a conduit for connecting to an operational catheter, and which includes a length of suction tubing 14*a* having an aspiration catheter connector 14*b* at or proximate to a terminal end thereof.

In the depicted embodiment, a clot catcher 15 according to an embodiment of the invention is provided advantageously in a form of an integrally incorporated sub-component of pump system 10. A blood collection chamber 16 is provided below a porous filter/strainer (not shown in FIGS. 1A and 1B, but can be best seen for example in FIGS. 4A and 4B). A transparent lid closure atop clot catcher 15 is optionally provided (not shown) and is advantageously openable or removable to facilitate removal of a collected clot or clots for detailed analysis.

Figure 2:
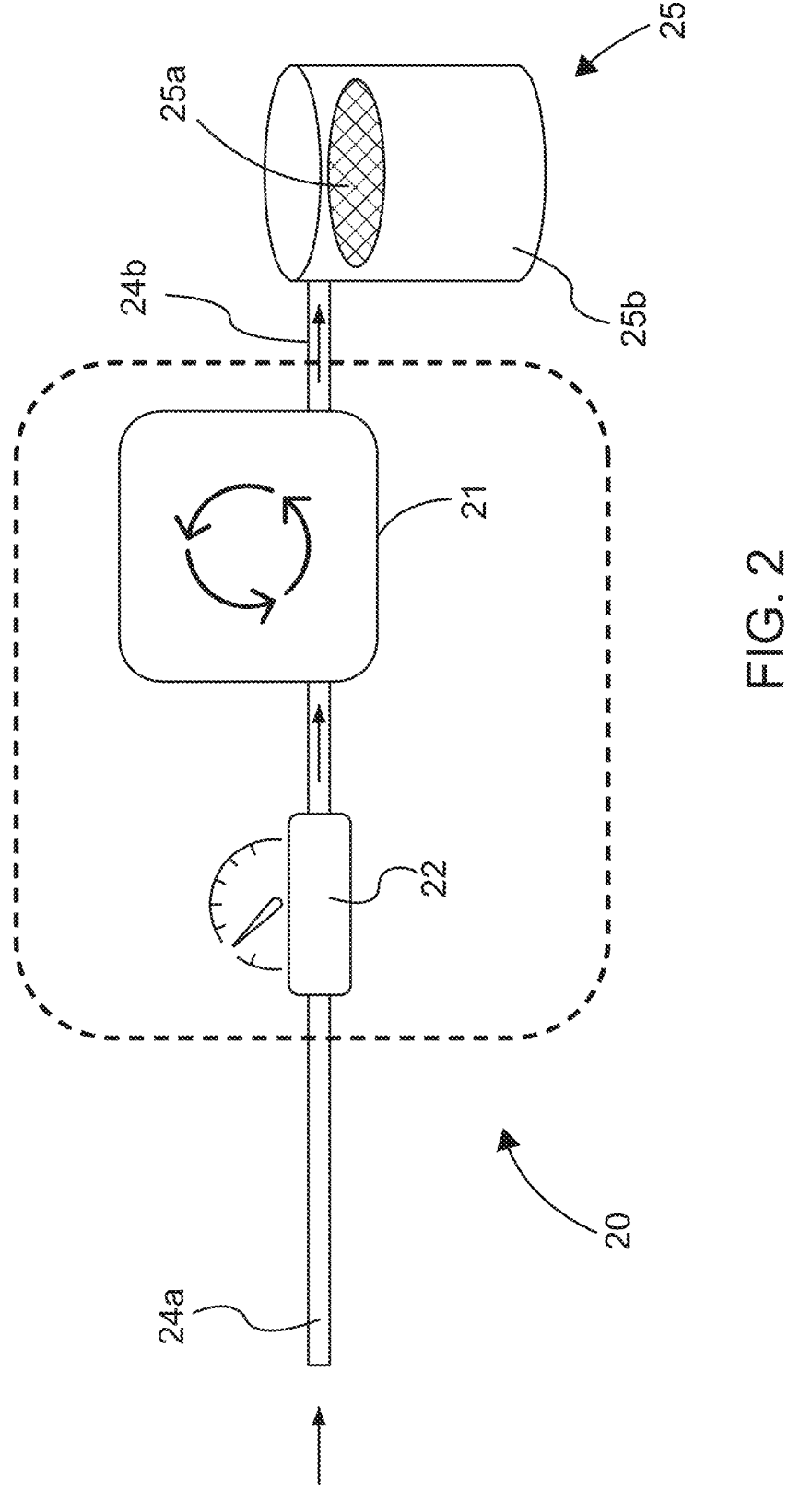
FIG. 2 depicts a schematic representation of core components of a system according to an embodiment of the present invention in which the clot catcher is located separate from a pump and control system.
Figure 3:
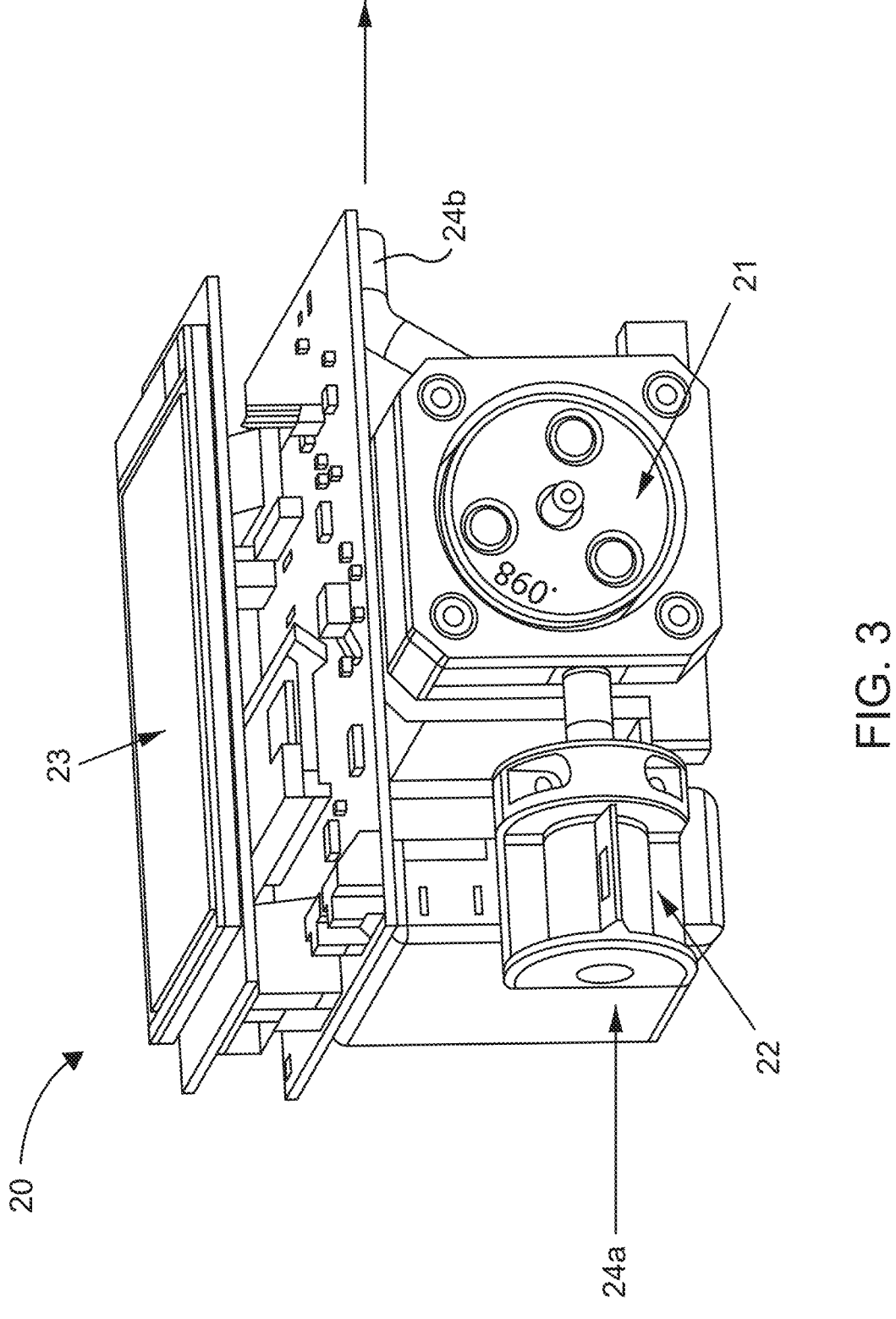
FIG. 3 is a perspective view of an example of a pump system connected to a clot catcher which is located separate from a pump and control system as schematically represented in FIG. 2 according to an embodiment of the invention.

Rather than providing a clot catcher as an integrated portion of a pump system housing as module of pump system 10 according generally to the previously described embodiment of the invention, an alternative embodiment includes a clot catcher provided as an element separate from the pump system, and as depicted schematically in FIG. 2 and as shown in side perspective in FIG. 3.

As shown, pump system 20 comprises a pump 21 and an optional pressure sensor 22. An inlet 24*a* leading from and communicative with a patient treatment catheter (not shown) is connected to pump system 20. Blood collected via inlet 24*a* is transferred via an outlet 24*b* from pump 21 to a separate clot catcher 25 comprising a porous strainer 25*a*, generally horizontally oriented, through which blood drains into a lower portion of a container/canister 25*b* (blood collection chamber), retainably depositing any collected clot or clots atop strainer 25*a*.

The pump system 20 according generally to the depicted embodiment of FIG. 2 is shown in side perspective in FIG. 3. Pump system 20 includes pump 21 configured advantageously in a form which includes a peristaltic pump, the advantageously system 20, is provided with a pressure sensor 22, and optionally further comprises an LCD touch screen for further control of the system. Inlet 23*a* leading from, and communicative with, a patient catheter (not shown) is connected to outlet 23*b* from pump 21 and are also identified in FIG. 3.

Figure 4A:
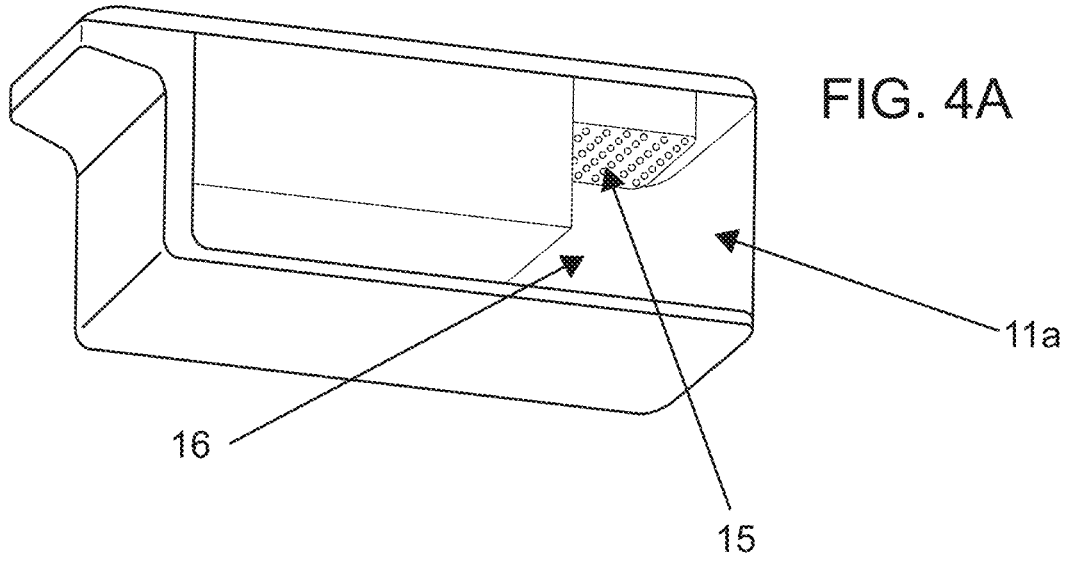
FIG. 4A is a side perspective exemplary view of a pump system in general accordance with FIGS. 1A and 1B being shown with a top housing portion removed exposing the integrated clot catcher blood collection compartment.
Figure 4B:
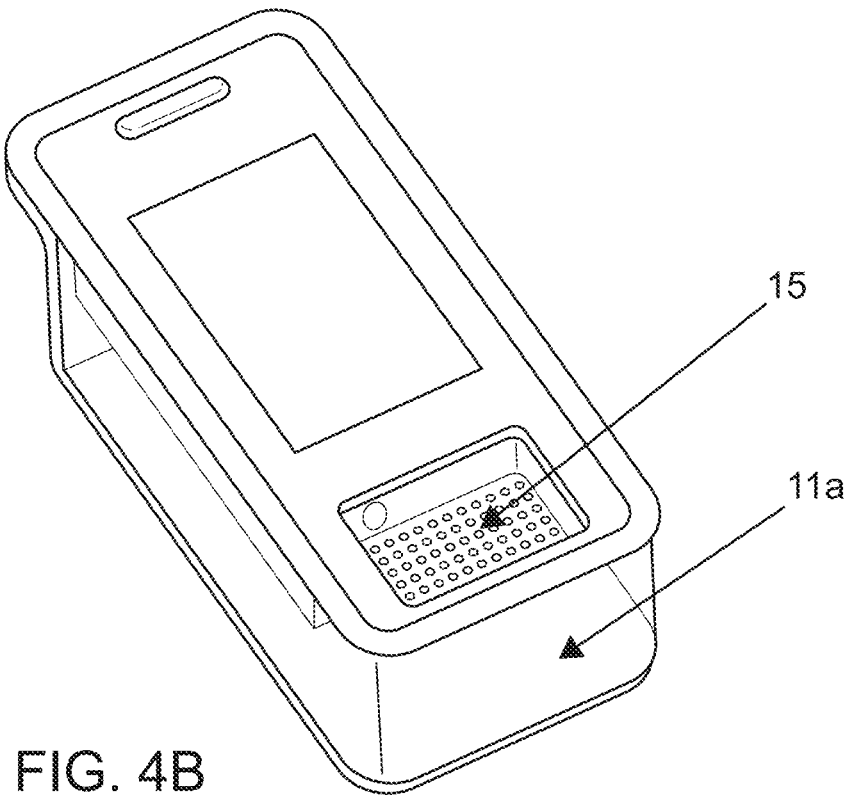
FIG. 4B is a top perspective view of the pump system of FIG. 4A.

FIGS. 4A and 4B depict generally the embodiment previously described with reference to FIGS. 1A and 1B, with top housing portion omitted to allow a view of the interior of the integrated clot catcher. In such embodiment, clot catcher 15 is built into a collection compartment 16, of advantageously sterile design. A retrieved clot or clots stay above a perforated strainer provided in the clot catcher 15 co-compartment, while blood collected with the clot(s) drains into the blood collection chamber below, allowing the operator to have the ability within convenient reach and observational scope, the ability to examine the clot(s) and to ascertain a type and composition thereof, as well as the amount of blood withdrawn, to provide therapeutic and diagnostic information.

Since there are well known procedures for determining the compositional nature of various types of clots involved and which are readily understood by those skilled in the art, further discussions of a determination and analysis of such are not discussed further as being deemed unnecessary for purposes herein.

It is noted that while the use of the clot catcher (clot capture device) described herein will most certainly find application in treating human patients, it will be also applicable in veterinary fields of practice, and such use is contemplated to be within the scope of the invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention.

What is claimed is:

1. An apparatus, comprising:
   a thrombectomy pump;
   a housing including a collection chamber and a pump chamber, the thrombectomy pump coupled within the pump chamber;
   an aspiration tube extending from the thrombectomy pump within the pump chamber;
   a clot retainer coupled to the housing within the collection chamber, the clot retainer having a porous surface to allow liquid to flow through the surface and into the collection chamber; and
   a lid removably coupled to the housing to cover the clot retainer, the lid including a transparent portion to allow viewing of the clot retainer through the lid,
   a portion of the aspiration tube extending horizontally and in fluid communication with an outlet port in a side wall of the collection chamber such that the liquid flows into the collection chamber above the porous surface of the clot retainer, through the clot retainer, and into the collection chamber.

2. The apparatus of claim 1, wherein:
   the housing has a base surface, the surface of the clot retainer is disposed at a first distance from the base surface of the housing, and
   the outlet port in the side wall of the collection chamber is at a second distance from the base surface, the second distance being greater than the first distance.

3. The apparatus of claim 1, wherein:
   the thrombectomy pump is coupled to the aspiration tube to provide fluid communication between the thrombectomy pump and the collection chamber.

4. The apparatus of claim 1, wherein:
   the collection chamber surrounds at least a portion of the pump chamber.

5. The apparatus of claim 1, wherein:
   the collection chamber has a volume of at least 1000 cubic centimeters.

6. The apparatus of claim 1, wherein the thrombectomy pump is a peristaltic pump.

7. An apparatus, comprising:

a housing including a first housing portion and a second housing portion, the second housing portion defining a pump chamber and a collection chamber, the collection chamber at least partially encircles the pump chamber;

a pump assembly disposed within the pump chamber, the pump assembly including an inlet port configured to be coupled to a catheter and an outlet port in fluid communication with the collection chamber;

the pump assembly including a pump, a sensor, and a controller;

the first housing portion coupled to the second housing portion and enclosing the pump chamber; and a touch screen coupled to the first housing portion and operably coupled to the controller.

8. The apparatus of claim 7, further comprising:

a lid removably coupled to the second housing portion and enclosing at least a portion of the collection chamber.

9. The apparatus of claim 7, wherein:

the collection chamber includes a clot cavity, the clot cavity in direct fluid communication with the outlet port.

10. The apparatus of claim 9, further comprising:

a clot retainer having a porous bottom surface to allow liquid to flow through the bottom surface and into the collection chamber.

11. The apparatus of claim 10, wherein:

a lid disposable over the clot retainer, the lid including a transparent portion to allow viewing of the clot retainer through the lid.

12. The apparatus of claim 10, wherein:

the housing has a base surface, the outlet port being positioned at a first distance relative to the base surface, the bottom surface of the clot retainer being disposed at a second distance from the base surface, the first distance being greater than the second distance.

13. The apparatus of claim 10, wherein:

the outlet port extends parallel with the bottom surface of the clot retainer.

14. The apparatus of claim 7, further comprising:

an aspiration tube coupled to the pump within the pump chamber, a portion of the aspiration tube extending within the outlet port and in fluid communication with the collection chamber.

15. The apparatus of claim 7, wherein the pump is a peristaltic pump.

16. The apparatus of claim 7, wherein:

the collection chamber has a volume of at least 1000 cubic centimeters.

* * * * *